United States Patent [19]
Voorhees

[11] 4,134,153
[45] Jan. 16, 1979

[54] THROW-AWAY EAR PROTECTOR

[76] Inventor: Donna S. Voorhees, 2081 Garfias Dr., Pasadena, Calif. 91104

[21] Appl. No.: 597,203

[22] Filed: Jul. 18, 1975

[51] Int. Cl.² .......................................... A41D 21/00
[52] U.S. Cl. ............................................. 2/174; 2/209; 2/243 R; 128/151
[58] Field of Search .......... 2/174, 209, 243 B, 243 R, 2/49 R, 410; 128/151

[56] References Cited

U.S. PATENT DOCUMENTS

| | | | |
|---|---|---|---|
| 2,142,282 | 1/1939 | Norton | 2/174 |
| 3,001,646 | 9/1961 | Cooper | 2/49 R |
| 3,229,875 | 1/1966 | Stoller | 2/49 X |
| 3,525,103 | 8/1970 | Yonan | 2/174 |
| 3,823,713 | 7/1974 | Shah | 2/209 X |
| 3,841,325 | 10/1974 | Pickard | 2/209 X |

FOREIGN PATENT DOCUMENTS

| | | | |
|---|---|---|---|
| 52582 | 1/1937 | Denmark | 2/209 |
| 776779 | 11/1934 | France | 2/209 |

Primary Examiner—Peter Nerbun
Attorney, Agent, or Firm—Sellers and Brace

[57] ABSTRACT

A throw-away ear protector readily assembled about the base of the human ear to preclude entry of foreign matter or fluid into the ear, and comprising a plaque of film-like impervious material. An opening centrally of the plaque is encircled with pressure sensitive adhesive for securing the plaque to the skin at the base of the ear. The outer portions of the plaque are readily gathered and maintained secured in gathered condition until the risk of harm has passed following which the protector can be removed and discarded.

8 Claims, 4 Drawing Figures

THROW-AWAY EAR PROTECTOR

This invention relates to an ear protector, comprising a plaque of impervious, supple film-like material readily assembled about the ear in a fluid-tight manner and discarded after a single use.

Many persons are afflicted with conditions of the ear by virtue of which it is of paramount importance to provide a highly reliable safeguard against the entry of foreign matter of either a fluid or solid nature. Because of such afflictions, it is risky and hazardous to expose the ear to a wide range of weather conditions or to enter areas containing dust-laden air or moist air. Other common hazards include those encountered in bathing, taking showers, or washing the scalp, or having the hair dressed by beauticians unfamiliar with the risks incurred by persons so afflicted.

Various proposals have been made heretofore to safeguard against the foregoing and other hazards but these proposals are subject to various shortcomings and disadvantages avoided by the present invention. In general, one typical form of prior art device is specially molded to accommodate the complex contours of the ear. Other proposals involve attempts to fabricate an ear protector from sheet stock. Most of these proposals utilize adhesive material to hold the protector assembled to the skull at the base of the ear. Examples of molded ear protectors are disclosed in to Yonan U.S. Pat. Nos. 3,525,103 and another to Bogart 2,763,869. However, the size and contour of the ear varies widely and this is also true of the contour of the skull adjacent the base of the ear. Any molded structure has very substantial thickness with the result that it is difficult if not impossible to provide assurance that the protector can be deformed and maintained sealed to the widely varying shapes of the skull in a leakproof manner. U.S. Pat. No. to Schurmeier 1,255,800 attempts to surmount this problem by providing a protector having an unusually wide flexible base flange sealable to the skull surface with rubber cement. However, the hair line normally extends fairly close to the base of the ear with the result that the Schurmeier mounting flange must be applied over substantial portions of the hair adjacent the ear. Pickard 3,841,325 seeks to avoid the high labor and manufacturing costs involved in the manufacture of molded ear protectors by utilizing a deep tubular bag of flexible material sealed closed at one end and fully open at the other. One sidewall of this bag is provided with an ear receiving opening encircled with adhesive material. After the opening in the side of this bag has been assembled over the ear the open end of the bag is tied in a knot releasable to permit reopening for inspection of the ear. Such a protector involves costly hand operations in its manufacture, utilizes much excess material, and is bulky and space-consuming after assembly to the ear.

Each of the foregoing protective devices and others of similar nature must be specially fabricated or molded at considerable cost in equipment, materials and labor and is subject to various other disadvantages avoided by the present invention.

This invention provides a highly reliable ear protector which is far simpler in structure, less costly to manufacture, and readily stored compactly and in a sanitary manner until ready for use. The protector comprises a single layer plaque of supple film-like impervious material. The plaque is provided with a central opening readily accommodating the base of the ear and the outer portions of which are snugly gatherable about the ear and then secured by a rubber band, a knot or a tie strip. The plaque can be assembled about either ear by rotating the plaque, if necessary about the axis of its opening. Preferably the plaques are connected together by a row of perforations in end relation and are storable in a roll enclosed within a dispensing container from which individual ones may be removed as needed. A masking strip for the adhesive conceals and protects the adhesive until the plaque is ready for use. A quantity of the protectors are readily storable in a container sized to fit within a garment pocket or in a woman's purse.

Accordingly, it is a primary object of the present invention to provide an improved, inexpensive, highly reliable throw-away protector for enclosing the ear and to a method of making the same and which protector comprises a flat plaque of film material the peripheral portions of which are readily gatherable about the ear.

Another object of the invention is the provision of an ear protector formed from a single plaque of impervious supple film having a central opening accommodating the base of the ear and coated with a ring of pressure sensitive material to hold the plaque sealed to the skull about the base of the ear.

Another object of the invention is the provision of a method of making an improved ear protector a multiplicity of which are separably attached to one another in a continuous strip of flexible impervious film material.

These and other more specific objects will appear upon reading the following specification and claims and upon considering in connection therewith the attached drawing to which they relate.

Referring now to the drawing in which a preferred embodiment of the invention is illustrated:

Figure 1:
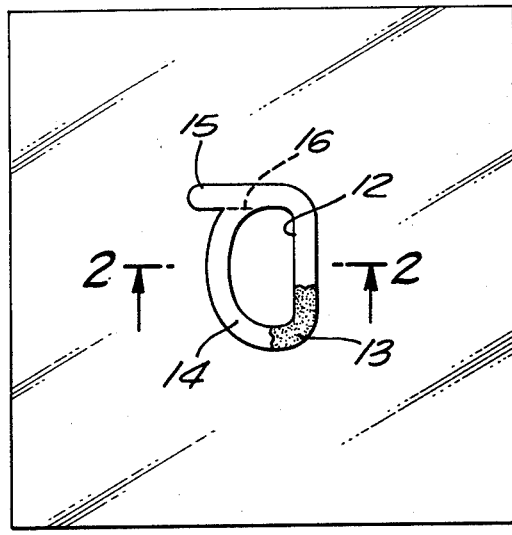
FIG. 1 is a plan view of an illustrative embodiment of the ear protector embodying the principles of the invention while outstretched and before assembly to the ear.

Referring initially more particularly to FIG. 1, there is shown a single ear protector 10 prior to being assembled about an ear. This protector as there shown comprises a generally square plaque 11 of supple film-like impervious material such as any suitable plastic material of high flexibility, softness, as for example polyethylene film having any suitable thickness as, for example, two or three mils. It will be understood that plastic films of a wide variety of compositions are suitable in practicing this invention. Desirably the plaque is transparent to facilitate its assembly about the ear.

The central portion of plaque 11 is an opening 12 shaped and sized to fit about the base of ears of a wide range of sizes. As shown, opening 12 is generally D-shaped but, if desired, it may be formed by a plurality of generally radial slits radiating from a common intersection point generally centrally of the opening and terminating adjacent the periphery of opening 12.

Surrounding the ear receiving opening 12 is a narrow band of pressure sensitive adhesive 13 well known to persons skilled in the adhesive art as nonreactive with or harmful to the skin, or other parts of the body. One suitable adhesive having these properties is obtainable from the Mercury Label Company and is identified by that supplier by the designators FC-290. This adhesive is firmly adherent to plaque 11 and is preferably protected until ready for application to the user's skin by a masking member 14 of well known material readily peelable from the adhesive at the time of use. Mask 14 preferably includes a pull tab 15 readily grasped between the forefinger and thumb. The mask preferably includes a row of perforations 16 crosswise of the mask adjacent one peripheral edge of tang 15 to facilitate severance of the mask during the initial stage of its removal.

Protectors 10 are preferably made in a continuous strip with the adjacent ends of contiguous protectors lightly adjoined to one another by a row of perforations 18 extending crosswise of the plaques midway between the ear receiving openings 12, 12. This arrangement greatly facilitates and simplifies the manufacture of the plaques following which the continuous strip of plaques is coiled into a roll and stored in a sealed container 20 having a dispensing slit 21. An individual protector 10 is readily dispensed and separated from the remainder along the line of perforations 18.

The mode of assembling a separated plaque about the ear will be readily apparent from the foregoing description of the plaque. The user first separates one of the plaques 11 from the continuous strip and then removes the masking cover 14 from the adhesive by grasping the pull tab 15 and severing the mask along the line of perforations 16. The outstretched plaque is then placed about the ear while the hair is held withdrawn from the base of the ear. The straight side of opening 12 is placed foremost and the ear is gathered and slipped through opening 12 following which the exposed adhesive is pressed firmly against the skull. Particular care is taken to assure that the complete ring of adhesive is pressed into firm contact with the skin including in particular the shallow trough-like depression commonly emanating from the opening along the forwardly facing side thereof. This trough-like depression should be firmly sealed to the juxtaposed surface of the protector to safeguard against the possibility of moisture or other foreign material entering the ear.

The rounded upper portion of the D-shaped opening 12 is seated against the juxtaposed portion of the ear to minimize the portion of the adhesive which may come in contact with the hair. Once the operator is assured that the adhesive is sealed to the skull the peripheral portions of the plaque are gathered and twisted snugly about the ear and secured in place either by making a knot in the gathered material or preferably by assembling a ductile wire tie strip 22 about the gathered portions of the plaque and twisting it taut. It will be apparent that all excess material is easily gathered snugly about the ear in this manner after which a hairdresser may proceed to dress the hair without interference from the protector. No moisture or foreign material can enter the ear and the protector remains firmly and reliably assembled to the scalp until the user wishes to remove it. The protector may then be simply peeled away from the scalp without need for undoing the tie wire following which the protector is discarded.

Figure 3:
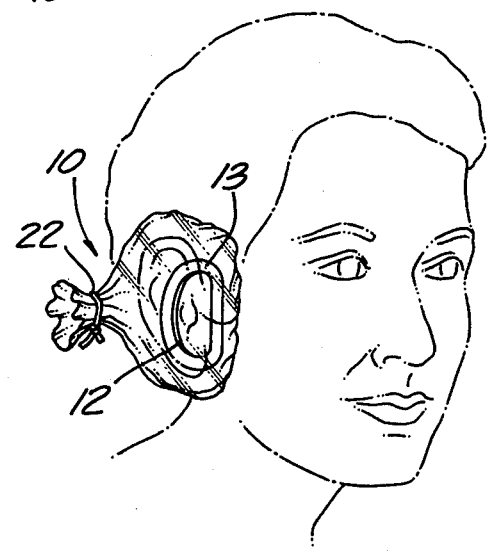
FIG. 3 is a perspective view showing the ear protector assembled about the ear.
Figure 2:
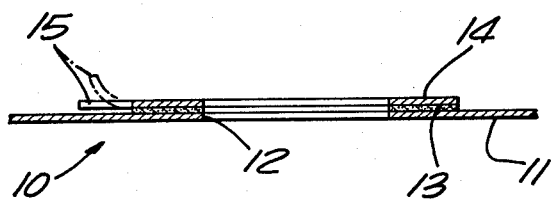
FIG. 2 is a cross-sectional view on an enlarged scale taken along line 2—2 of FIG. 1 and showing the thickness of the parts on an exaggerated scale.
Figure 4:
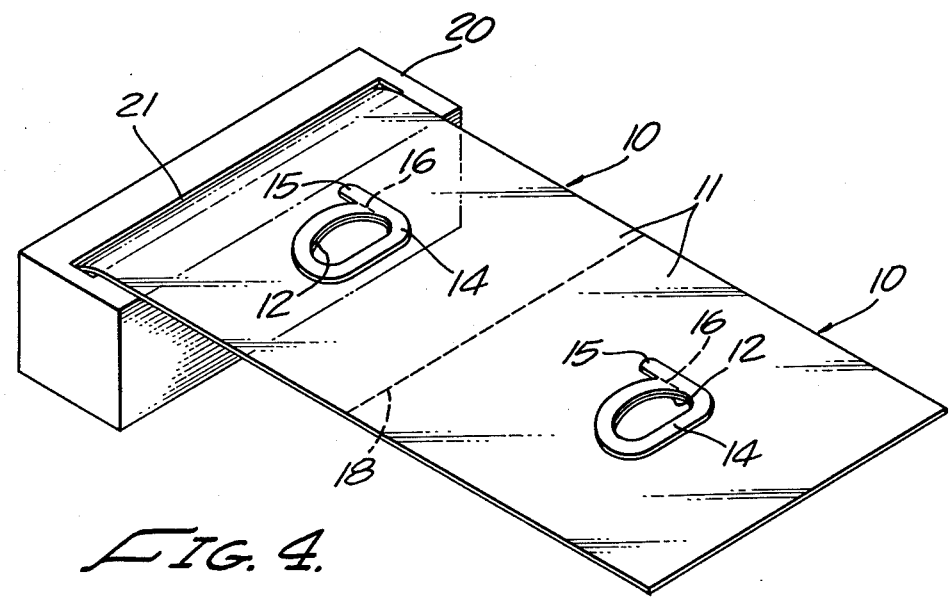
FIG. 4 is a perspective view of a continuous strip of the ear protector plaques connected to one another by a row of perforations and with one end of the strip projecting through the dispensing opening of a container therefor.

It will be understood that both ears are readily protected by the same procedure, it merely being necessary to rotate the protector through 180° about the axis of its central opening to assemble it about the opposite from that shown in FIG. 3. Opening 12 may be sufficiently large to accommodate a wide range of ear sizes thereby making it unnecessary to provide a special size for each user.

While the particular throw-away ear protector herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

I claim:

1. A single-use throw-away ear protector comprising a single outstretched non-tubular plaque of supple impervious film having an opening generally centrally thereof, said opening being sized to receive the base of the human ear and encircled by a band of pressure sensitive adhesive masked until applied to the ear by a protective cover, and the perimeter portions of said plaque being snugly gatherable about the ear and securable tightly together thereby to provide a waterproof enclosure for the ear to exclude moisture from entering said enclosure and the ear so long as assembled about the ear with said pressure sensitive adhesive pressed against the skull about the ear base.

2. A throw-away ear protector as defined in claim 1 characterized in that said film has a single elongated opening therein to receive the ear and is adapted to be assembled over either ear with said band of adhesive facing the skull.

3. A throw-away ear protector as defined in claim 1 characterized in that a plurality of said plaques are attached to one another in a continuous strip and separable from one another as needed along a row of perforations extending crosswise of said strip generally centrally between said ear receiving openings.

4. A throw-away ear protector as defined in claim 3 characterized in that said continuous strip of individual plaques are coiled one upon another in a roll, and a carton enclosing said roll of ear protector plaques having a dispensing opening for said plaques lengthwise of one face thereof.

5. That method of making a single-use throwaway ear protector which comprises: at least partially separating bulk supple film-like impervious sheet material into individual one-layer plaques each sufficiently large to receive the human ear and to be gathered and secured about the ear to provide a fluid-tight enclosure therefor, forming an opening generally centrally of each plaque to receive the base of the ear, applying a ring of pressure sensitive adhesive about the ear receiving opening effective to anchor and seal said protector to the skull in a closed ring encircling the base of the ear, and covering said ring of adhesive with a readily removable protective mask until said ear protector is about to be assembled over the ear.

6. That method defined in claim 5 characterized in the steps of separating said plaques from bulk film-like material so that said plaques are arranged in a continuous strip and connected to one another only by rows of perforations extending crosswise of said strip thereby to facilitate complete separation of each plaque from the remainder thereof.

7. That method defined in claim 5 characterized in the step of storing each ear protectors in a roll enclosed within a carton having an elongated dispensing slot along one face thereof.

8. A throw-away ear protector as defined in claim 1 characterized in that said perimeter portions of said plaque are free of means attached thereto for securing the perimeter portions of said plaque gathered about the ear.

* * * * *

UNITED STATES PATENT OFFICE
CERTIFICATE OF CORRECTION

Patent No. 4,134,153    Dated January 16, 1979

Inventor(s) Donna S. Voorhees

It is certified that error appears in the above-identified patent and that said Letters Patent are hereby corrected as shown below:

Claim 1, line 7, "the" should read -- all --.

Claim 1, line 7, before "plaque" -- outstretched -- should be inserted.

Claim 1, line 8, before "snugly" -- thereafter -- should be inserted.

Claim 1, line 8, after "ear" -- from all sides thereof -- should be inserted.

Claim 1, line 9, after "together" -- generally coaxillay of the ear opening -- should be inserted.

Claim 5, line 4, before "individual" -- a plurality of -- should be inserted.

Claim 5, line 4, after "one-layer" -- outstretched -- should be inserted.

Claim 5, line 5, after "ear" -- while outstretched -- should be inserted.

Claim 5, line 5, before "gathered" -- thereafter -- should be inserted.

Claim 5, line 5, after "gathered" -- from all sides of the ear -- should be inserted.

Claim 5, line 6, "about" should be deleted.

UNITED STATES PATENT OFFICE
CERTIFICATE OF CORRECTION

Patent No. 4,134,153             Dated January 16, 1979

Inventor(s) Donna S. Voorhees

It is certified that error appears in the above-identified patent and that said Letters Patent are hereby corrected as shown below:

Claim 5, line 6, before "the ear" -- closed generally opposite -- should be inserted.

Claim 5, line 6, after "the ear" -- opening -- should be inserted.

Claim 7, line 2, "each" should read -- said --.

*Signed and Sealed this*

*Twenty-second* Day of *May 1979*

[SEAL]

*Attest:*

RUTH C. MASON
*Attesting Officer*

DONALD W. BANNER
*Commissioner of Patents and Trademarks*